(12) United States Patent
Oda

(10) Patent No.: US 7,607,778 B2
(45) Date of Patent: Oct. 27, 2009

(54) OPTOTYPE PRESENTING APPARATUS

(75) Inventor: Tatefumi Oda, Nukata-gun (JP)

(73) Assignee: Nidek Co., Ltd., Gamagori (JP)

( * ) Notice: Subject to any disclaimer, the term of this patent is extended or adjusted under 35 U.S.C. 154(b) by 0 days.

(21) Appl. No.: 12/213,401

(22) Filed: Jun. 19, 2008

(65) Prior Publication Data

US 2008/0316428 A1 Dec. 25, 2008

(30) Foreign Application Priority Data

Jun. 22, 2007 (JP) ............................. 2007-165277

(51) Int. Cl.
*A61B 3/02* (2006.01)
(52) U.S. Cl. ....................... 351/240; 351/242
(58) Field of Classification Search ................ 351/222, 351/239, 240, 242, 243
See application file for complete search history.

(56) References Cited

U.S. PATENT DOCUMENTS

| | | | |
|---|---|---|---|
| 5,026,151 A * | 6/1991 | Waltuck et al. ............. | 351/246 |
| 5,331,358 A * | 7/1994 | Schurle et al. .............. | 351/232 |
| 5,638,082 A | 6/1997 | Grimm | |
| 6,011,580 A | 1/2000 | Hattori et al. | |

FOREIGN PATENT DOCUMENTS

| | | |
|---|---|---|
| DE | 10 2004 032 819 A1 | 2/2006 |
| EP | 0 595 023 A1 | 5/1994 |
| EP | 0 911 792 A2 | 4/1999 |
| JP | A-7-322304 | 12/1995 |
| JP | A-2002-311385 | 10/2002 |
| JP | A-2006-42978 | 2/2006 |
| KR | 2002-0037157 A | 5/2002 |

* cited by examiner

*Primary Examiner*—Huy K Mai
(74) *Attorney, Agent, or Firm*—Oliff & Berridge, PLC

(57) ABSTRACT

An optotype presenting apparatus capable of performing a test with accuracy by minimizing differences in manners an optotype is seen by examinees which result from differences in height of eyes among the examinees comprising a display unit comprising pixels having color filters arranged in a longitudinal direction, a polarization optical member comprising first and second optical regions in the form of a longitudinal line corresponding to the arrangement of the pixels which are alternately arranged in a lateral direction, the regions converting light from the display unit into light having polarizing axes perpendicular to each other, an optotype selecting unit, and a display control unit controlling the pixels corresponding to the first regions to display first optotypes of the optotype to be presented to a right or left eye, and controls the pixels corresponding to the second regions to display second optotypes thereof to be presented to the other eye.

5 Claims, 6 Drawing Sheets

OPTOTYPE PRESENTING APPARATUS

BACKGROUND OF THE INVENTION

1. Field of the Invention

The present invention relates to an optotype presenting apparatus which presents an optotype such as an optotype for a visual acuity test and an optotype for a binocular vision test.

2. Description of Related Art

Conventionally, there is known an optotype presenting apparatus of a display type such that various optotypes are displayed on a screen of a display unit (see Japanese Patent Application Unexamined Publication No. 2006-42978). In this optotype presenting apparatus, when presenting binocular optotypes for a binocular vision test to an examinee, a technique for displaying a three-dimensional image can be used in order to present different optotypes to a right eye and a left eye of the examinee (see Japanese Patent Application Unexamined Publication No. 2002-311385, and U.S. Pat. No. 5,638,082 corresponding to Japanese Patent Application Unexamined Publication No. Hei 07-322304).

FIG. 6 is a longitudinal sectional view of a color liquid crystal display unit 30 and a polarization optical member 50 placed in front of the display unit 30 in an optotype presenting apparatus which uses the same technique for displaying a three-dimensional image as that of Japanese Patent Application Unexamined Publication No. 2002-311385. In front of a liquid crystal 31 of the display unit 30, an oriented film 32b, a transparent electrode 33b, a color filter 40 in which R, G and B filters are arranged in each of pixels 42, a transparent supporting member 34b, and a polarizing plate 35b are placed in order. The polarization optical member 50 is placed in front of the polarizing plate 35b and comprises optical regions 55a and 55b which are in the form of a lateral line (laterally long) corresponding to the arrangement of the pixels 42 in a lateral direction (a horizontal direction), and are alternately arranged in a longitudinal direction (a vertical direction). Light from the display unit 30 is converted by the optical regions 55a and 55b so that light passing through the optical regions 55a and light passing through the optical regions 55b have polarizing axes perpendicular to each other. By placing a polarizing filter which has a polarizing axis coinciding with the polarizing axis of the light passing through the optical regions 55a in front of either one of the examinee's right and left eyes, and placing a polarizing filter which has a polarizing axis coinciding with the polarizing axis of the light passing through the optical regions 55b in front of the other eye, different optotypes are presented to the right eye and the left eye, whereby a binocular vision test can be performed.

Light in a direction of the normal P01 via the pixels 42 is converted by the optical regions 55a and 55b so that light passing through the optical regions 55a and light passing through the optical regions 55b have polarizing axes perpendicular to each other. Here, the light via the pixels 42 heads also for a direction P02 other than the direction of the normal P01 and passes as leakage light through the optical regions 55a and 55b alternately arranged adjacent to each other in the longitudinal direction, because there is a gap having a thickness of the supporting member 34b (about 1 mm) between the pixels 42 and the polarization optical member 50. When the examinee looks the display unit 30 on which the binocular optotype is displayed, substantially from the direction of the normal 201, the leakage light hardly reaches the eye, so that the test can be performed with accuracy. However, when the examinee cannot see the display unit 30 on which the binocular optotype is displayed from the direction of the normal P01, the test cannot be performed with accuracy because the leakage light tends to reach the eye.

SUMMARY OF THE INVENTION

An object of the invention is to provide an optotype presenting apparatus capable of performing a test with accuracy by minimizing differences in manners an optotype for a binocular vision test is seen by examinees, which result from differences in height of eyes among the examinees.

To achieve the objects and in accordance with the purpose of the present invention, an optotype presenting apparatus comprises a display unit comprising pixels arranged in longitudinal and lateral directions in which R, G and B color filters are arranged in order in the longitudinal direction, a polarization optical member placed in front of the display unit which comprises first and second optical regions in the form of a longitudinal line corresponding to the arrangement of the pixels of the display unit in the longitudinal direction, which are alternately arranged in the lateral direction, the first and second optical regions arranged to convert light from the display unit into light having polarizing axes perpendicular to each other, an optotype selecting unit comprising optotype selecting switches including a switch for selecting a binocular optotype for a binocular vision test, and a display control unit which controls the pixels corresponding to the first optical regions to display first optotypes of the binocular optotype which are to be presented to either one of right and left eyes of an examinee, and controls the pixels corresponding to the second optical regions to display second optotypes of the binocular optotype which are to be presented to the other eye.

Additional objects and advantages of the invention are set forth in the description which follows, are obvious from the description, or may be learned by practicing the invention. The objects and advantages of the invention may be realized and attained by optotype presenting apparatus in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
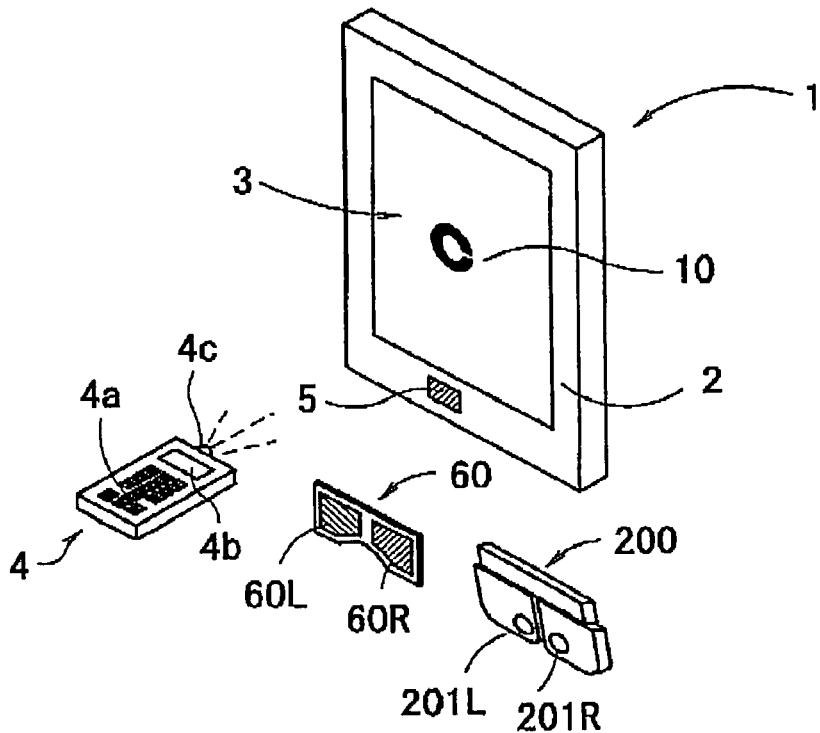
FIG. 1 is a schematic external view showing an optotype presenting apparatus according to a preferred embodiment of the present invention.

A detailed description of one preferred embodiment of an optotype presenting apparatus embodied by the present invention is provided below with reference to the accompanying drawings. FIG. 1 is a schematic external view showing an optotype presenting apparatus according to a preferred embodiment of the present invention. An optotype presenting apparatus 1 comprises a housing 2, and an optotype presenting unit 3 placed on a front surface of the housing 2. The presenting unit 3 comprises a screen large enough to display an optotype 10 such as an optotype for a visual acuity test and an optotype for a binocular vision test of a given size even when the presenting unit 3 is placed at a far distance for a test, e.g., a distance of 5 m from an examinee. The size of the screen is preferably 19 inches or more. In addition, the housing 2 is preferably shaped thinly so as to be hanged on (secured to) a wall.

At a lower portion on the front surface of the housing 2, a receiving portion 5 is provided, which receives a communication signal as infrared light from a remote control 4 defining an optotype selecting unit. The optotype 10 to be presented on the presenting unit 3 is changed by operating the remote control 4. Polarization spectacles 60 comprising polarizing filters 60L and 60R which have polarizing axes perpendicular to each other are placed in front of right and left eyes of the examinee at the time of a binocular vision test. The polarizing filter 60L for the left eye has the polarizing axis oriented in the direction of 45 degrees, and the polarizing filter 60R for the right eye has the polarizing axis oriented in the direction of 135 degrees. If a subjective eye refractive power measurement apparatus (a phoropter) 200 in which corrective lenses such as spherical lenses are switched to be placed in right and left test windows (201R, 201L) is used, polarizing filters having polarizing axes perpendicular to each other which are similar to the polarizing filters (60R, 60L) provided to the polarization spectacles 60 are switched and placed in the right and left test windows (201R, 201L) at the time of the binocular vision test.

Figure 2:
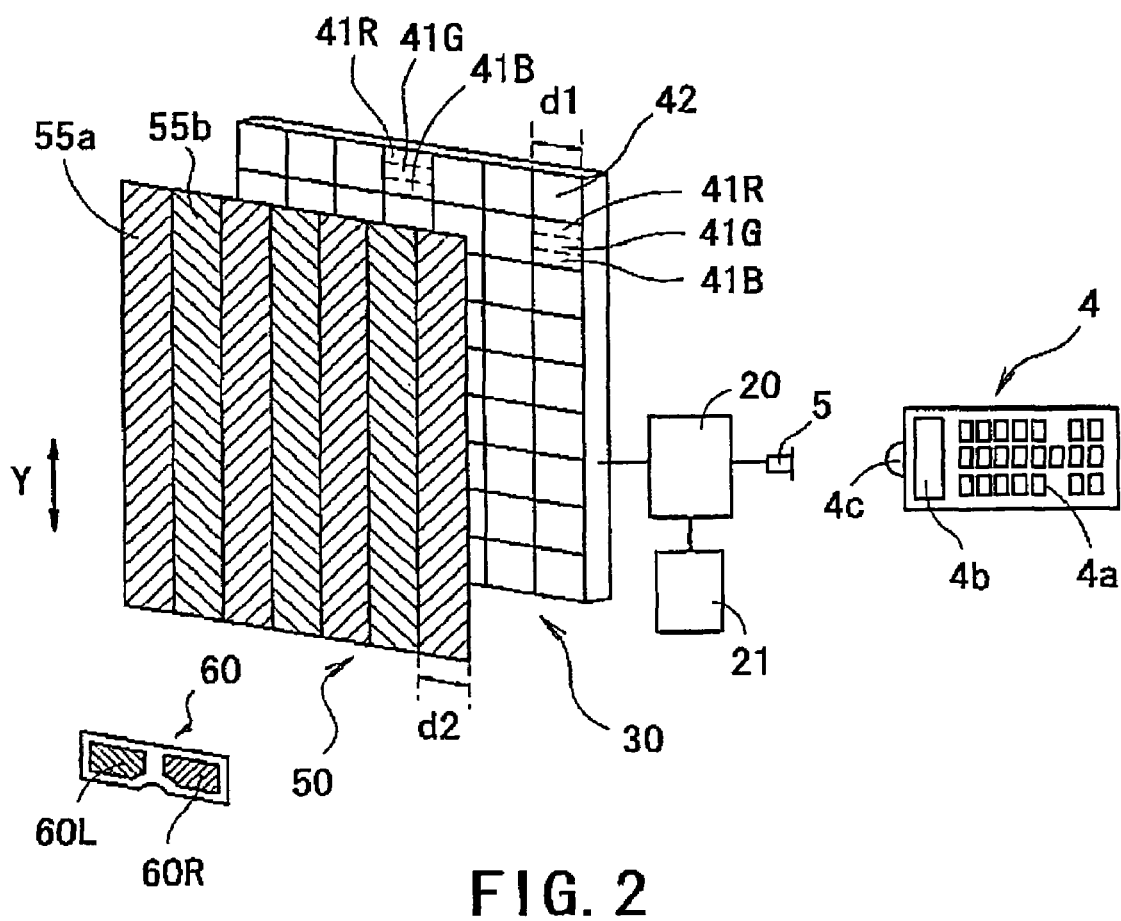
FIG. 2 is a view showing a schematic configuration of an optotype presenting unit and a schematic block diagram of a control system of the optotype presenting apparatus.

FIG. 2 is a view showing a schematic configuration of the optotype presenting unit 3 and a schematic block diagram of a control system of the optotype presenting apparatus 1. The optotype presenting unit 3 comprises a color liquid crystal display unit 30 and a sheet-like polarization optical member 50 placed in front of the display unit 30. The polarization optical member 50 is large enough to cover at least an optotype presenting region on the display unit 30. The display unit 30 and the receiving portion 5 are connected to a control unit 20. The control unit 20 comprises a memory 21 which stores data on various optotypes, a decoder circuit which decodes a command signal from the remote control 4, and other constituent elements. When a command signal for switching the optotypes or other signals from the remote control 4 is inputted to the control unit 20, the control unit 20 performs display control of pixels 42.

The remote control 4 comprises a plurality of switches 4a for selecting an optotype to be displayed on the display unit 30, a liquid crystal display portion 4b which displays the selected optotype and its information, and a transmitting portion 4c which transmits the communication signal as the infrared light based on a switch signal of the remote control 4.

Figure 3A:
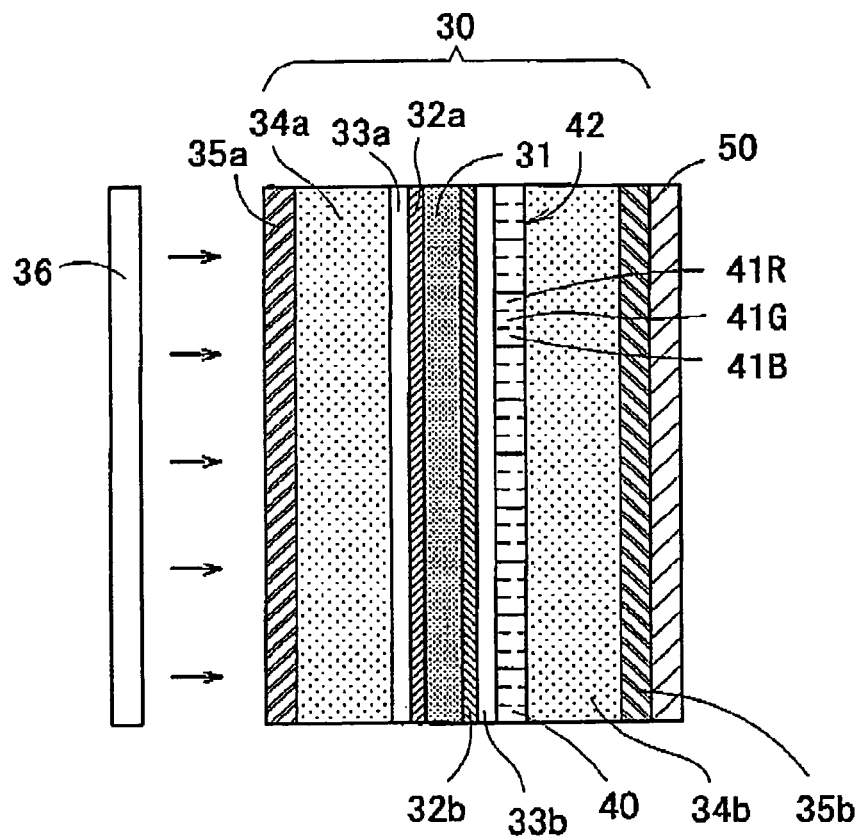
FIG. 3A is a longitudinal sectional view of a color liquid crystal display unit and a polarization optical member of the optotype presenting unit.

FIG. 3A is a longitudinal sectional view of the display unit 30 and the polarization optical member 50. Behind a liquid crystal 31 which is placed almost in the middle of the display unit 30, an oriented film 32a, a transparent electrode 33a, a transparent supporting member 34a, a first polarizing plate 35a having a polarizing axis in a horizontal direction, and a backlight 36 are placed in this order. In front of the liquid crystal 31, an oriented film 32b, a transparent electrode 33b, a color filter 40 in which R, G and B filters are arranged in each of the pixels 42, a transparent supporting member 34b, and a second polarizing plate 35b having a polarizing axis in a vertical direction are placed in this order The second polarizing plate 35b is placed so that the polarizing axis thereof is perpendicular to the polarizing axis of the first polarizing plate 35a. A glass plate or a cellulose acetate butyrate (CAB) plate having a thickness of about 1 mm is preferably used as the supporting members 34a and 34b. The polarization optical member 50 is attached to a front surface of the second polarizing plate 35b. The directions of the polarizing axes of the first polarizing plate 35a and the second polarizing plate 35b are not limited to the horizontal and vertical directions, and it is sufficient for the directions to be perpendicular to each other.

Figure 3B:
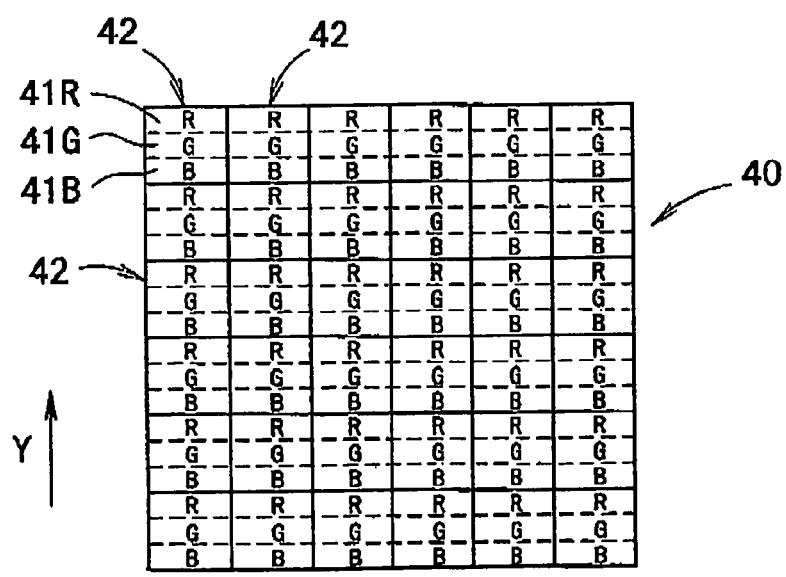
FIG. 3B is a view showing an arrangement of R, G and B filters of a color filter.

FIG. 3B is a view showing the arrangement of the B, G and R filters of the color filter 40. The display unit 30 has the pixels 42 which are regularly arranged in the longitudinal and lateral directions. In the color filter 40, an R (red) filter 41R, a G (green) filter 41G, and a B (blue) filter 41B are arranged in the longitudinal direction (a Y-direction) as a set in each of the pixels 42. The transparent electrode 33a has electrodes independently controllable which are placed so as to correspond to the arrangement of the filters 41R, 41G and 41B. Accordingly, by independently controlling the electrodes of the transparent electrode 33a, an arrangement of liquid crystal molecules of the liquid crystal 31 is changed. Therefore, when light passes through the first polarizing plate 35a, the liquid crystal 31 and the second polarizing plate 35b, light intensity corresponding to each of the R, G and B filters (41R, 41G, 41B) can be changed, allowing color of each of the pixels 42 to be freely presented.

As the display unit 30, a display unit which is commercially available can be used. The commercially available display unit is normally used as a laterally long display unit having for example 1280×1024 pixels in a state where R, G and B filters are arranged in order in the lateral direction. Thus, when using the commercially available display unit as the display unit 30, the commercially available display unit is placed longitudinally long by being rotated 90 degrees with respect to the commercially available display unit in the normal usage state according to a conventional art so that the R, G and B filters are arranged in order in the longitudinal direction as shown in FIG. 3B.

There are other arrangement manners of the R, G and B filters such as a mosaic arrangement such that the R, G, B filters are arranged diagonally by color, and any arrangement manner may be used.

Next, the configuration of the polarization optical member 50 is described below. Linearly polarized light having a polarizing axis (a polarizing plane) in a predetermined direction (the vertical direction, the horizontal direction, or an oblique direction of 45 degrees) is emitted from the display unit 30 via the second polarizing panel 35b. In the preferred embodiment of the present invention, light having a polarizing axis in the vertical direction is emitted. The polarization optical member 50 comprises optical regions 55a and 55b in the form of a longitudinal line (longitudinally long) which are alternately arranged in the lateral direction. The optical regions 55a and 55b have functions of converting light into linearly polarized light having polarizing axes perpendicular to each other when transmitting the light from the display unit 30. In the preferred embodiment of the present invention, a member having a function equivalent to that of a half wavelength plate which makes a phase difference is used as the polarization optical member 50. As is well known, the half wavelength plate is arranged to rotate a vibration direction of incident light by 2×θ degrees when the incident light with a polarization plane enters at θ degree(s) with respect to a fast axis (or a slow axis) of the half wavelength plate. In other words, the half wavelength plate has a function of rotating a direction of the polarizing axis of the incident light by inclining a direction of its optically principal axis that is the fast axis (or the slow axis) with respect to the direction of the polarizing axis of the incident light, and has a property of being capable of maintaining light intensity of the incident light.

In FIG. 2, the first polarization regions 55a in the form of a longitudinal line (longitudinally long) define optical regions for the right eye, and a direction of the optically principal axis thereof is arranged so that the incident light is converted into light having a polarizing axis direction which coincides with the polarizing axis direction of 135 degrees of the polarizing filter 60R for the right eye. The second polarization regions 55b in the form of a longitudinal line (longitudinally long) define optical regions for the left eye, and a direction of the optically principal axis thereof is arranged so that the incident light is converted into light having a polarizing axis direction which coincides with the polarizing axis direction of 45 degrees of the polarizing filter 60L for the left eye. When looking at the display on the presenting unit 3 through the polarizing filters 60R and 60L placed in front of the right and left eyes, the examinee visually perceives by the left eye only the light from the optical regions 55b which is capable of passing through the polarizing filter 60L, while the light from the optical regions 55a is blocked by the polarizing filter 60L and is not visually perceived by the left eye. In contrast, the examinee visually perceives by the right eye only the light from the optical regions 55a which is capable of passing through the polarizing filter 60R, while the light from the optical regions 55b is blocked by the polarizing filter 60R and is not visually perceived by the right eye. Therefore, different optotypes can be presented to the right eye and the left eye.

If the display unit 30 is arranged to emit light having a polarizing axis direction of 45 degrees, an optical member which does not have a function of making a phase difference and transmits the light maintaining the polarizing axis direction may be used for the optical regions 55.

In the preferred embodiment of the present invention, a width d2 of the optical regions 55a and 55b is made approximately equivalent to a width d1 of the pixels 42 of the display unit 30. However, if the optical regions 55a and 55b are as small as not to be distinguished from each other by the examinee's eyes at the distance for the test, the optical regions 55a and 55b may be arranged to cover a region of an integral multiple of the width d1 of the pixels 42.

In addition, in the preferred embodiment of the present invention, a liquid crystal display unit is used as the display unit 30. However, a plasma display unit, an organic EL display unit, an SED display unit and other display units may be used as the display unit 30. When light exiting from a display unit other than the liquid crystal display unit does not have a property of linearly polarized light, a polarizing plate is preferably placed between the display unit 30 and the polarization optical member 50.

Alternatively, it is also preferable that in the polarization optical member 55 polarizing plates having a polarizing axis direction of 45 degrees are placed in the optical regions 55a, and polarizing plates having a polarizing axis direction of 135 degrees are placed in the optical regions 55b as described in U.S. Pat. No. 5,638,082.

Next, the binocular vision test is described in which the polarization spectacles 60 are used. As the optotype for a binocular vision test, an optotype for an aniseikonia test, an optotype for a heterophoria test, an optotype for a binocular balance test, and an optotype for a stereoscopic vision test are prepared, and hereinafter, a description of the binocular vision test is provided referring to an optotype 100 for a stereoscopic vision test shown in FIG. 4. In the optotype 100, an optotype 101a at the upper left and an optotype 102a at the lower left of the screen are visually perceived by a right eye ER via the polarizing filter 60R. An optotype 101b at the upper right and an optotype 102b at the lower right of the screen are visually perceived by a left eye EL via the polarizing filter 60L. The optotypes 101a and 101b have the same shape and the same color, and are displayed apart in the horizontal direction such that a predetermined stereoparallax is produced. In addition, the optotypes 102a and 102b have the same shape and the same color, and are displayed apart in the horizontal direction such that a predetermined stereoparallax is produced. An optotype 103 positioned almost at the center of the screen is a fixation point that defines an optotype for a fusion stimulus which is visually perceived by both the right eye ER and the left eye EL.

In the optotype 100, when an examinee with normal stereoscopic acuity can see the optotypes 101a and 102a by the right eye ER and the optotypes 101b and 102b by the left eye EL, an optotype 101 and an optotype 102 are visually perceived which appear to float in mid-air respectively at distances L1 and L2 from the optotype 103. The stereoscopic test is performed by checking if the examinee can recognize floating amounts for the distances L1 and L2.

Figure 5:
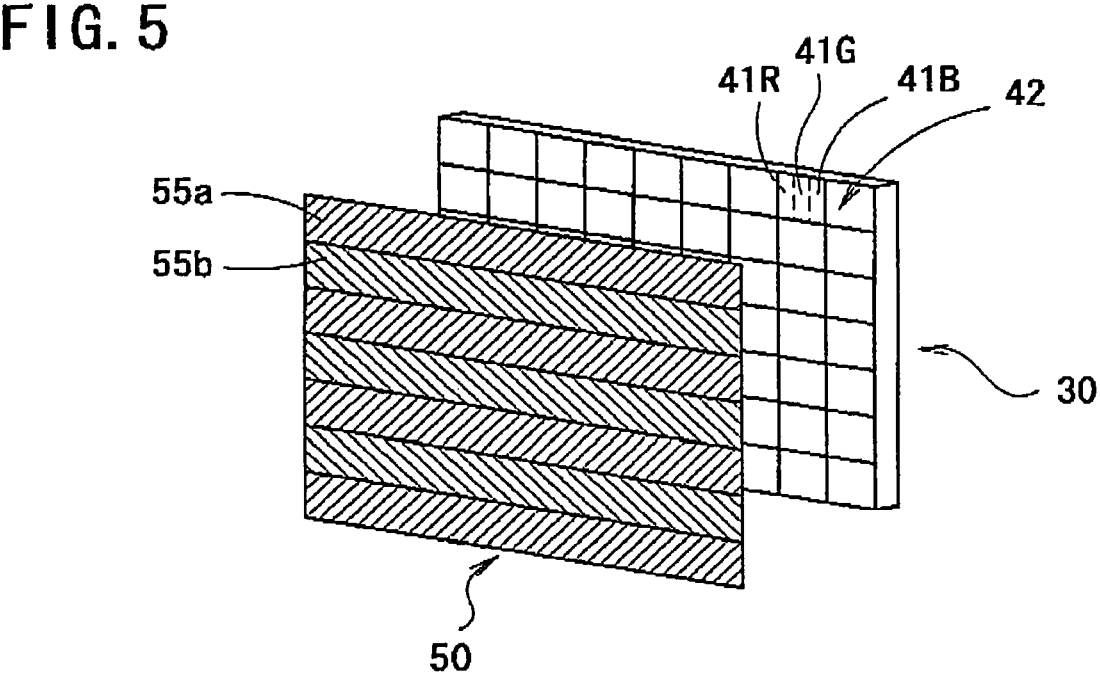
FIG. 5 is a view showing a placement according to a conventional art of the color liquid crystal display unit and the polarization optical member of the optotype presenting unit.
Figure 6:
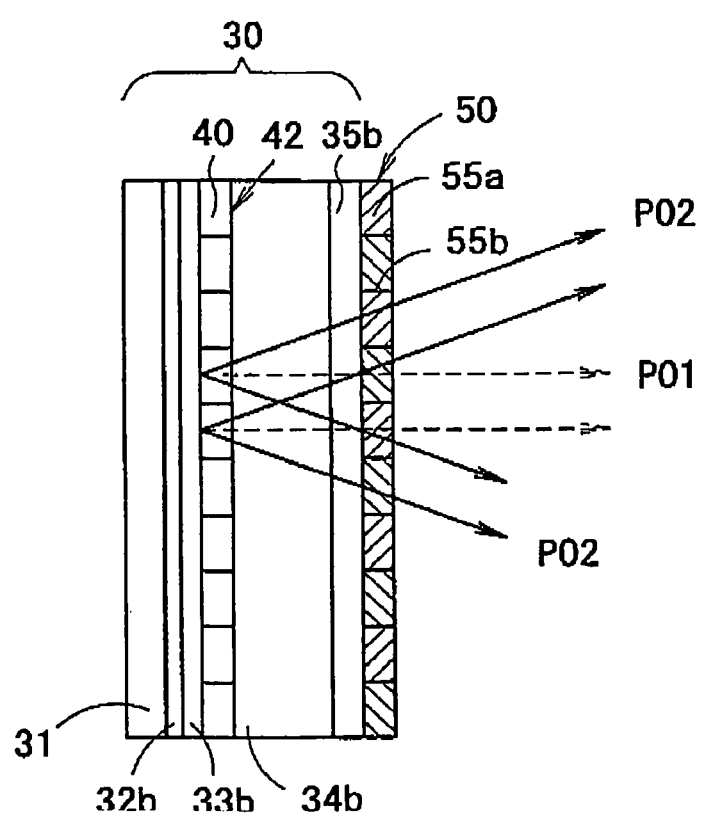
FIG. 6 is a view showing a longitudinal sectional view of the color liquid crystal display unit and the polarization optical member of the optotype presenting unit placed according to the conventional art.

FIG. 5 shows a case, in the binocular vision test performed by presenting the optotypes as above, where the filters 41R, 41G and 41B are arranged in order in the lateral direction, and the optical regions 55a and 55b in the form of a lateral line (laterally long) a width of which is approximately equivalent to a height of the pixels 42 are alternately arranged in the longitudinal direction as in the normal state of the conventional use of the display unit 30. In this case, as described in the Description of the Related Art, if the position of the eyes is very high or low because the examinee is very tall or small, the examinee cannot see the optotypes from the optical regions 55a and 55b separately by the right and left eyes via the polarization spectacles 60, so that the binocular vision test cannot be performed with accuracy. When the test distance is set to 5 m, if the position of the eyes differs by 20 cm or more, the examinee cannot see the optotypes separately by the right and left eyes.

However, this problem due to the difference in position of the eyes can be solved by alternately arranging the optical regions 55a and 55b in the form of the longitudinal line in the lateral direction as shown in FIG. 2. In other words, by employing the arrangement in FIG. 2, the light from each of the pixels 42 passes through either the optical regions 55a or 55b in the longitudinal direction, and thereby the optotypes from the optical regions 55a and 55b can be seen separately by the right and left eyes via the polarization spectacles 60 even when the position of the eyes is very high or low.

In this case, a similar problem as described above is expected to occur in the lateral direction because the optical regions 55a and 55b in the form of the longitudinal line are alternately arranged in the lateral direction. However, since visual acuity tests and binocular vision tests are performed by placing the examinee's face almost right in front of the presenting unit 3 and there is little difference in eye positions in the lateral direction among different examinees, the above-described arrangement can be practically used without problems.

It is found that heavy "blurring (exuding) of color" occurs when the filters 41R, 41G and 41B are arranged in order in the lateral direction in the display 30 similarly to the conventional arrangement while the optical regions 55a and 55b in the form of the longitudinal line are alternately arranged in the lateral direction.

Figure 7A:
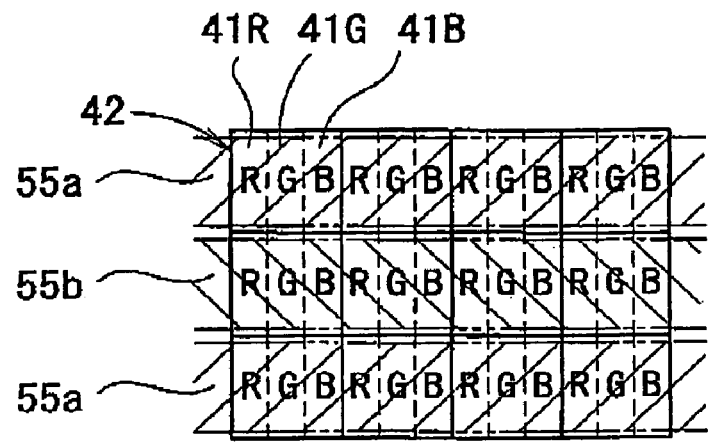
FIGS. 7A, 7B and 7C are views showing relations between arrangements of the polarization optical member with respect to arrangements of the R, G and B filters and occurrences of a "blurring (exuding) of color"
Figure 7B:
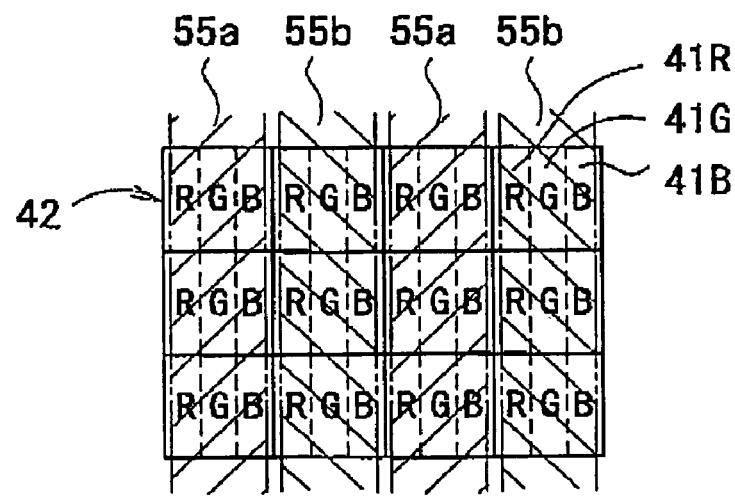

In FIG. 7A, the filters 41R, 41G and 41B are arranged in order in the lateral direction, and the optical regions 55a and 55b in the form of the lateral line are alternately arranged in the longitudinal direction. In FIG. 7B, the filter 41R, 41G and 41B are arranged in order in the lateral direction similarly to the arrangement shown in FIG. 7A, while the optical regions 55a and 55b in the form of the longitudinal line are alternately arranged in the lateral direction. It should be noted that though the optical regions 55a and 55b are prepared so as to be adjacent to each other, they are shown as being separated in FIGS. 7A and 7B for the sake of convenience in explanation.

Because there is a gap having a thickness of the supporting member 34b between the color filter 40 that is a light-emitting portion and the polarization optical member 50, the light leaks out of the optical regions 55a and 55b alternately arranged adjacent to each other. In FIG. 7A, all of the filters 41R, 41G and 41B are placed adjacent to each other at boundaries between the optical regions 55a and 55b, and thereby a color of light reaching the eye becomes uniform even when the light leaks out. In FIG. 7B, on the other hand, only the filters 41B and 41R are placed adjacent to each other at boundaries between the optical regions 55a and 55b, and thereby a color of light reaching the eye becomes nonuniform, which causes the "blurring of color" to be visually perceived. For example, a portion which should look white could look colored.

Figure 7C:
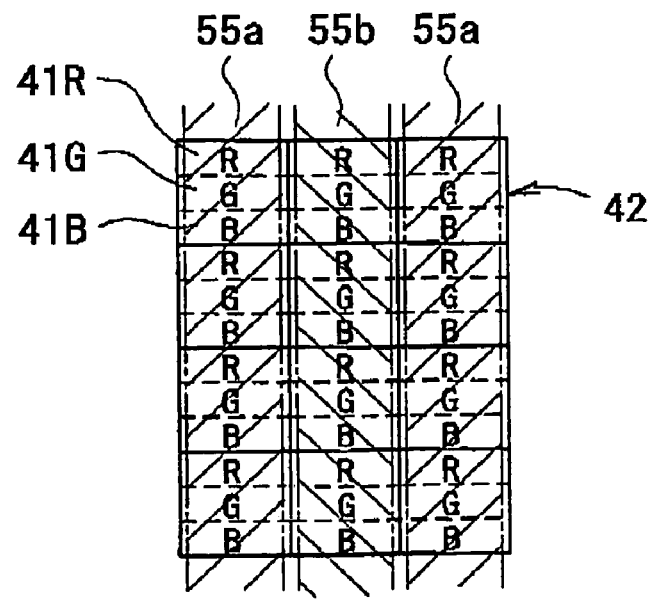

Hence, when the optical regions 55a and 55b in the form of the longitudinal line are alternately arranged in the lateral direction, the filters 41R, 41G and 41B are arranged in order in the longitudinal direction as shown in FIG. 7C. Consequently, all of the filters 41R, 41G and 41B are placed adjacent to each other at the boundaries between the optical regions 55a and 55b, and thereby the color becomes uniform as in the case of the arrangement shown in FIG. 7A. Therefore, the "blurring of color" can be suppressed.

Figure 4:
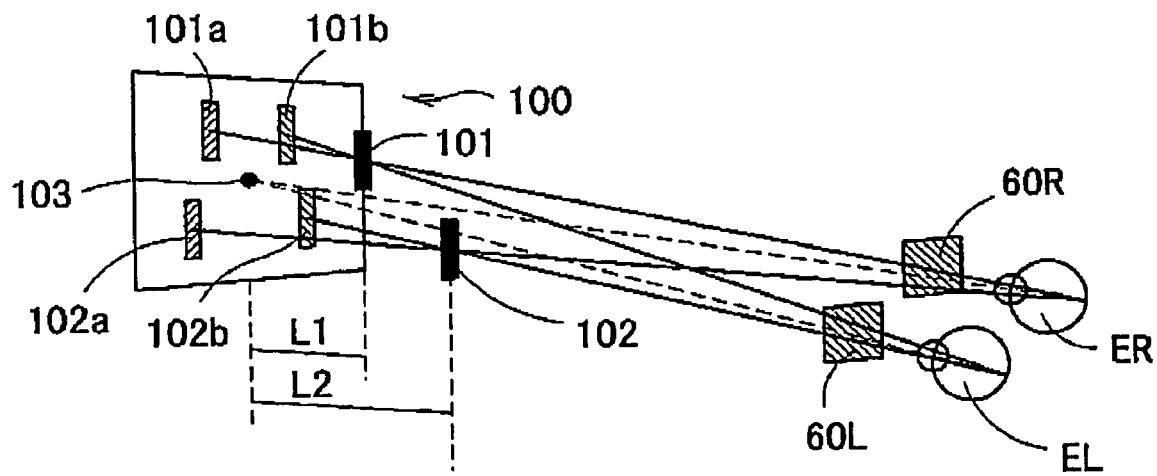
FIG. 4 is a view showing an example of a binocular optotype for a binocular vision test.
Figure 8A:
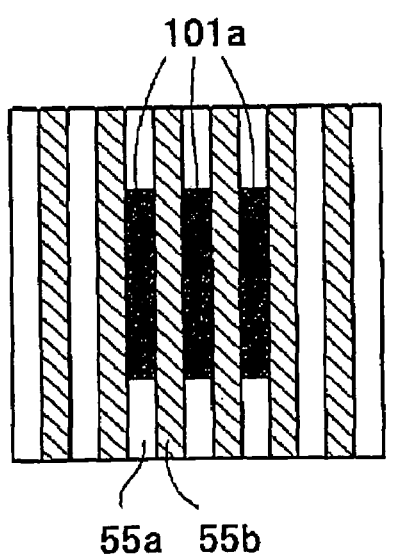
FIGS. 8A and 8B are views showing presenting states of the binocular optotype (states of visually perceiving the binocular optotype)
Figure 8B:
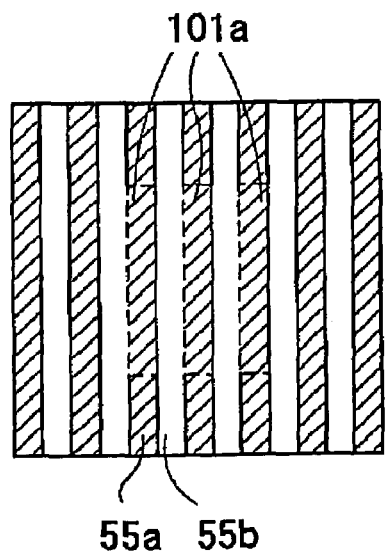

Next, a presenting state of the optotype for a binocular vision test brought by the placement of the display unit 30 and the polarization optical member 50 shown in FIG. 2 is described referring to the optotype 100 for a stereoscopic vision test shown in FIG. 4. FIG. 8A is a view showing a state where the optotype 101a presented by the presenting unit 3 shown in FIG. 4 is visually perceived by the right eye ER via the polarizing filter 60R. FIG. 8B is a view showing a state where the optotype 101a is visually perceived by the left eye EL via the polarizing filter 60L.

Because the optotype 101a is an optotype to be presented only to the right eye ER, display on the display unit 30 is controlled so that the optotype 101a is displayed in black only in the optical regions 55a. The display on the display unit 30 is also controlled so that portions other than the optotype 101a in the optical region 55a, and the optical regions 55b are displayed in white. In this case, the optotype light and the white light from the optical regions 55a pass through the polarizing filter 60R and reach the right eye ER, while the white light from the optical regions 55b is blocked by the polarizing filter 60R. Accordingly, the optical regions 55b in FIG. 8A are displayed in black. However, because the widths of the optical regions 55a and 55b are sufficiently narrow, and the white light from the optical regions 55a is intense, the optotype 101a against a white background is seen by the right eye ER.

Meanwhile, the white light from the optical regions 55b passes through the polarizing filter 60L and reaches the left eye EL, while the optotype light and the white light from the optical regions 55a are blocked by the polarizing filter 60L. Accordingly, the optical regions 55a in FIG. 8B are displayed in black. However, because the white light from the optical regions 55b is intense, only a white background without the optotype 101a is seen by the left eye EL.

Also for the other optotypes 101b, 102a, and 102b, the display on the display unit 30 is controlled similarly to the above manner. That is, the control unit 20 controls the pixels (42) corresponding to the optical regions 55a to display the optotypes 101a and 102a to be presented only to the right eye ER, and controls the pixels (42) corresponding to the optical regions 55b to display the optotypes 101b and 102b to be presented only to the left eye EL. With such display, the optotypes 101a and 102a are presented only to the right eye ER, and the optotypes 101b and 102b are presented only to the left eye EL.

Next, display of an optotype associated with the placement of the display unit 30 which is rotated 90 degrees clockwise or anticlockwise with respect to the display unit 30 in the usage state according to the conventional art is described.

Figure 9A:
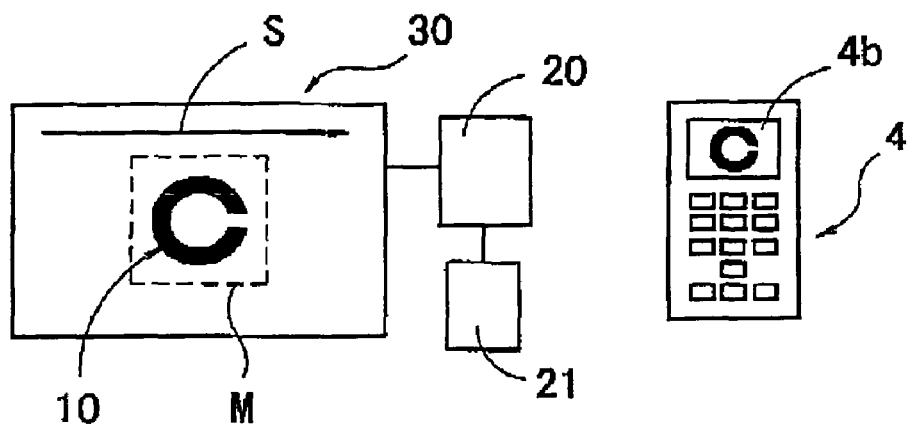
FIGS. 9A, 9B, 9C and 9D are views illustrating display of an optotype associated with the placement of the display unit which is rotated 90 degrees with respect to the display unit in a usage state according to the conventional art.

FIG. 9A is a view showing the display of the optotype made by the placement of the display unit 30 according to the conventional art, in which the optotype having an orientation is selected with the remote control 4. The memory 21 stores the optotype data. The control unit 20 reads the optotype data stored in the memory 21 based on an optotype selecting signal (a command signal for switching optotypes) generated with the switch 4a of the remote control 4, and controls the display unit 30 to display the optotype. In this example, a Landort-ring optotype 10 is displayed having a gap in the right side. Here, the display unit 30 is controlled by the control unit 20 such that display of the pixels (42) is scanned from left to right as shown by an arrow S. The memory 21 stores data on the Landort-ring optotype 10 having the gap in the right side, which corresponds to the scanning of the display. The R, G and B filters (41R, 41G, 41B) are arranged in order in the lateral direction.

Figure 9B:
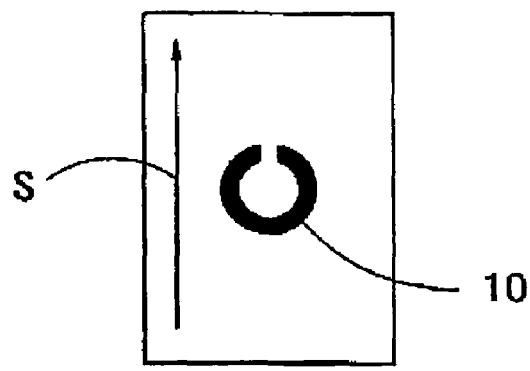

FIG. 9B is a view showing a case in which the display unit 30 shown in FIG. 9A is placed rotated 90 degrees anticlockwise so that the R, G and B filters (41R, 41G, 41B) are arranged in the longitudinal direction. In this case, the display of the pixels (42) is scanned from bottom to top. If the optotype data stored in the memory 21 and the display control by the control unit 20 are the same as those used for the display unit 30 shown in FIG. 9A, the Landor-ring optotype 10 is displayed having the gap in the upper side as shown in FIG. 9B. In this case, the visual acuity test cannot be performed with accuracy.

In order to make the display of the optotype having the orientation agree with the optotype selected with the remote control 4, the following two measures can be taken.

Figures 9C, 9D:
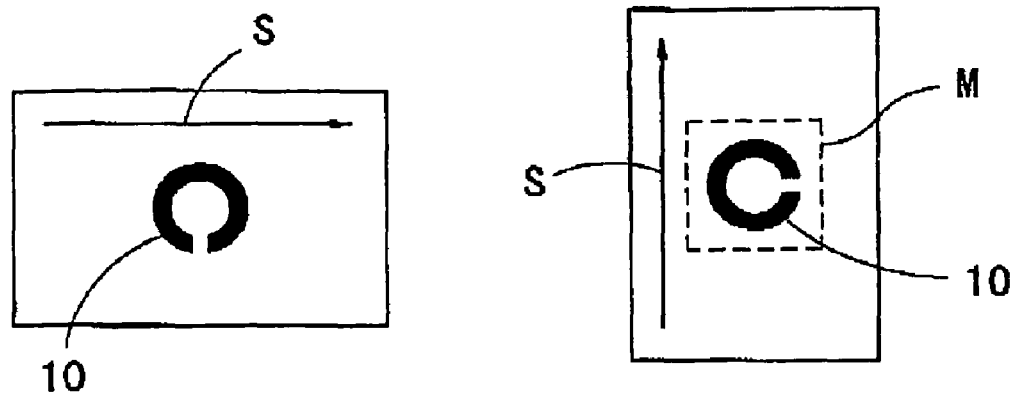

The first measure is to store in the memory 21 data on the optotype which is rotated in the opposite direction to the rotation direction of the display unit 30 by 90 degrees with respect to the optotype selected with the remote control 4 while associating the optotype data to the selected optotype. For example, if the display unit 30 is placed rotated 90 degrees anticlockwise, optotype data with which the optotype is displayed so as to have the gap in the bottom side in a state where the display unit 30 is not rotated (see FIG. 9C) is stored in the memory 21 while associating the optotype data with the optotype having the gap in the right side which is selected with the remote control 4. Accordingly, in a state where the display unit 30 is rotated, the optotype having the same orientation as that of the optotype selected with the remote control 4 (the optotype having the gap in the right side) is displayed as shown in FIG. 9D.

In the second measure, when the control unit 20 reads the optotype data from the memory 21 and controls the display unit 30 to display the optotype, the optotype is displayed rotated 90 degrees in the opposite direction to the rotation direction of the display unit 30. However, if the display on all the pixels (42) of the display unit 30 is rotated, the numbers of pixels (sizes) in the longitudinal and lateral directions do not coincide. Hence, the display on a region M only, for example, in which the optotype is included and the number of pixels (size) in the longitudinal direction coincides with the number of pixels (size) in the lateral direction (see FIG. 9A) is rotated 90 degrees in the opposite direction to the rotation direction of the display unit 30 (see FIG. 9D).

With the above-described measures, an appropriate test can be performed even when an optotype having an orientation is displayed. The optotype having an orientation includes an optotype for a binocular vision test in addition to an optotype for a visual acuity test.

The foregoing description of the preferred embodiment of the invention has been presented for purposes of illustration and description. It is not intended to be exhaustive or to limit the invention to the precise form disclosed, and modifications and variations are possible in the light of the above teachings or may be acquired from practice of the invention. The embodiment chosen and described in order to explain the principles of the invention and its practical application to enable one skilled in the art to utilize the invention in various embodiments and with various modifications as is suited to the particular use contemplated. It is intended that the scope of the invention be defined by the claims appended hereto, and their equivalents.

What is claimed is:

1. An optotype presenting apparatus comprising:
   a display unit comprising pixels arranged in longitudinal and lateral directions, in which R, G and B color filters are arranged in order in the longitudinal direction;
   a polarization optical member placed in front of the display unit, which comprises first and second optical regions in the form of a longitudinal line corresponding to the arrangement of the pixels of the display unit in the longitudinal direction, which are alternately arranged in the lateral direction, the first and second optical regions arranged to convert light from the display unit into light having polarizing axes perpendicular to each other;
   an optotype selecting unit comprising optotype selecting switches including a switch for selecting a binocular optotype for a binocular vision test; and
   a display control unit which controls the pixels corresponding to the first optical regions to display first optotypes of the binocular optotype which are to be presented to either one of right and left eyes of an examinee, and controls the pixels corresponding to the second optical regions to display second optotypes of the binocular optotype which are to be presented to the other eye.

2. The optotype presenting apparatus according to claim 1, wherein the display unit is a display unit in which display of pixels is scanned from left to right, and the pixels are arranged in the longitudinal and lateral directions, in which the R, G and B color filters are arranged in order in the lateral direction, the display unit placed rotated ninety degrees in one of clockwise and anticlockwise directions.

3. The optotype presenting apparatus according to claim 2, wherein when an optotype having an orientation is selected with the optotype selecting unit, the display control unit controls display on the display unit based on information on the rotation of the display unit so that the orientation of the optotype to be displayed on the display unit agrees with the orientation of the selected optotype.

4. The optotype presenting apparatus according to claim 1, wherein the display control unit comprises a memory which stores data on an optotype having an orientation which is to be displayed on the display unit, and reads the data on the optotype stored in the memory based on an optotype selecting signal from the optotype selecting unit, and controls the display unit to display the optotype.

5. The optotype presenting apparatus according to claim 4, wherein
   the display unit is a display unit in which display of pixels is scanned from left to right, and the pixels are arranged in the longitudinal and lateral directions, in which the R, G and B color filters are arranged in order in the lateral direction, the display unit placed rotated ninety degrees in one of clockwise and anticlockwise directions, and
   the display control unit controls a region in which the optotype is included and the number of pixels in the longitudinal direction coincides with the number of pixels in the lateral direction to be displayed rotated ninety degrees in the direction opposite to a direction of the rotation of the display unit so that the orientation of the optotype to be displayed on the display unit agrees with the orientation of the selected optotype.

* * * * *